US006858750B2

(12) United States Patent
Joshi et al.

(10) Patent No.: US 6,858,750 B2
(45) Date of Patent: Feb. 22, 2005

(54) USE OF FUMARIC ACID DERIVATIVES FOR TREATING MITOCHONDRIAL DISEASES

(75) Inventors: Rajendra Kumar Joshi, Zurich (CH); Hans-Peter Strebel, Lucerne (CH)

(73) Assignee: Fumapharm AG, Lucerne (CH)

(*) Notice: Subject to any disclaimer, the term of this patent is extended or adjusted under 35 U.S.C. 154(b) by 0 days.

(21) Appl. No.: 10/148,858

(22) PCT Filed: Dec. 11, 2000

(86) PCT No.: PCT/EP00/12504

§ 371 (c)(1),
(2), (4) Date: May 28, 2002

(87) PCT Pub. No.: WO01/51047

PCT Pub. Date: Jul. 19, 2001

(65) Prior Publication Data

US 2003/0013761 A1 Jan. 16, 2003

(30) Foreign Application Priority Data

Jan. 10, 2000 (DE) .......................................... 100 00 577

(51) Int. Cl.⁷ .............................................. C07C 69/52
(52) U.S. Cl. ........................ 560/205; 562/598; 514/557; 514/559; 514/578
(58) Field of Search .................................. 562/512, 598

(56) References Cited

U.S. PATENT DOCUMENTS

| | | |
|---|---|---|
| 3,832,287 A | 8/1974 | Gale et al. |
| 4,515,974 A | 5/1985 | Zecher et al. |
| 4,746,668 A | 5/1988 | Sato et al. |
| 4,851,439 A | 7/1989 | Speiser et al. |
| 4,959,389 A | 9/1990 | Speiser et al. |
| 5,149,695 A | 9/1992 | Speiser et al. |
| 5,214,196 A | 5/1993 | Blank |
| 5,242,905 A | 9/1993 | Blank |
| 5,359,128 A | 10/1994 | Blank |
| 5,424,332 A | 6/1995 | Speiser et al. |
| 5,451,667 A | 9/1995 | Speiser et al. |
| 5,538,968 A | 7/1996 | Chiesi et al. |
| 5,548,059 A | 8/1996 | Bayley et al. |
| 5,589,504 A | 12/1996 | Dannenberg et al. |
| 5,965,591 A | 10/1999 | Kojima et al. |
| 5,972,363 A | 10/1999 | Clikeman et al. |
| 6,005,116 A | 12/1999 | Kojima et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 | 1/2003 | Joshi et al. |
| 2002/0091087 A1 * | 7/2002 | Zhang et al. .................. 514/18 |
| 2003/0013761 A1 | 1/2003 | Joshi et al. |

FOREIGN PATENT DOCUMENTS

| | | |
|---|---|---|
| CA | 2248955 | 8/2001 |
| DE | 25 30 372 A1 | 1/1977 |
| DE | 26 21 214 A1 | 11/1977 |
| DE | 38 34794 A1 | 4/1990 |
| EP | 0 188 749 A2 | 7/1986 |
| EP | 0 312 697 A2 | 4/1989 |
| RU | 2132187 | 6/1999 |
| RU | 2136291 | 9/1999 |
| RU | 2160589 | 12/2000 |
| RU | 5189813 | 9/2002 |
| WO | WO 89/01930 A1 | 3/1989 |
| WO | WO 94/28883 | 12/1994 |
| WO | WO 95/25102 | 9/1995 |
| WO | WO 96/02244 | 2/1996 |
| WO | WO 96/27369 | 9/1996 |
| WO | WO 9713504 A1 | 4/1997 |
| WO | WO 97/48400 | 12/1997 |
| WO | WO 9748405 | 12/1997 |
| WO | WO 98/04290 | 2/1998 |
| WO | WO 98/27970 | 7/1998 |
| WO | WO 98/52549 | 11/1998 |
| WO | WO 99/21565 | 5/1999 |

OTHER PUBLICATIONS

Douglas C. Wallace, Science, vol. 283, Mar. 5, 1999.*

Amamoto, Toshiro, et al., "Effect of E–64, Thiol Protease Inhibitor on the Secondary Anti–SRBC Response In Vitro", Microbiol. Immunol., vol. 28(1), 1984, ppg 85–97.

Barrett, Alan J., et al., "L–trans–Epoxysuccinyl–leucylamido(4–guanidino) butane (E–64) and its analogues as inhibitors of cysteine proteinases including cathepsins B, H and L", Biochem. J., 1982, vol. 201, ppg 189–198.

Bellier, Bruno, et al., "Replacement of Glycine with Dicarbonyl and Related Moieties in Analogues of the C–Terminal Pentapeptide of Cholecystokinin: $CCK_2$ Agonists Displaying a Novel Binding Mode", J. Med. Chem., vol. 43, 2000, ppg 3614–3623.

Birch, A.J., et al., "Metabolites of *Aspergillus indicus*: The Structure and Some Aspects of the Biosynthesis of Dihydrocanadensolide", Aust. J. Chem., 1968, vol. 21, ppg 2775–2784.

Choo, Hea–Young, et al., "Design and Synthesis of $\alpha,\beta$–unsaturated Carbonyl Compounds as Potential ACE Inhibitors", Short Communication, Eur. J. Med. Chem., vol. 35, 2000, ppg 643–648.

(List continued on next page.)

*Primary Examiner*—Johann Richter
*Assistant Examiner*—Karl Puttlitz
(74) *Attorney, Agent, or Firm*—Sieberth & Patty, L.L.C.

(57) ABSTRACT

The present invention relates to the use of individual fumaric acid derivatives or mixtures thereof for preparing a pharmaceutical composition for treating mitochondrial diseases, especially for treating Parkinson's syndrome, Alzheimer's disease, Chorea Huntington disease, retinopathia pigmentosa and mitochondrial encephalomyopathy. Preferably, the fumaric acid derivative(s) is/are those selected from the group consisting of fumaric acid dialkyl esters or fumaric acid monoalkyl esters in the form of the free acid or a salt thereof.

22 Claims, No Drawings

OTHER PUBLICATIONS

Dethlefsen, L.A., "Toxic Effects of Acute Glutathione Depletion by Buthionine Sulfoximine and Dimethylfumarate on Murine Mammary Carcinoma Cells", Radiation Research, vol. 114, 1988, ppg 215–224.

Galpin, I.J., et al., "The Synthesis of an Insulin Active Site Analogue", Tetrahedron, vol. 39, No. 1, 1983, ppg 149–158.

Gerhard, Ute, et al., "The Free Energy Change of restricting A Bond Rotation in the Binding of Peptide Analogues to Vancomycin Group Antibiotics", Bioorganic & Medicinal Chemistry Letters, vol. 3, No. 5, 1993, ppg 803–808.

Gordon, G.B., et al., "Induction of NAD(P)H:quinone reductase in human peripheral blood lymphocytes", Carcinogenesis, vol. 12 (12), 1991, ppg 2393–2396.

Griehl, C., et al., "α–Aspartyl Peptides by Addition of Amines to N–Maleylamino Acid Derivatives", Chemistry of Peptides and Proteins, 1993, 5/6(pt. A), pp 99–103.

Hildebrandt, H., "Pschyrembel Klinisches Woerterbuch Ed. 258", Walter de Gruyter, New York, XP 002234302, p. 182, column 1, paragraph 2 and p. 1469, column 1, paragraph 16–column 2, paragraph 1. Not translated.

Hohenegger, M., et al., "Nephrotoxicity of Fumaric Acid Monoethylester (FA ME)", Advances in Experimental Medicine and Biology, US 1989, vol. 252, ppg 265–272.

Holroyd, S.E., et al., "Rational Design and Binding of Modified Cell–Wall Peptides to Vancomycin–Group Antibiotics: Factorising Free Energy Contributions to Binding", Tetrahedron, vol. 49, No. 41, 1993, ppg 9171–9182.

Kamiyama, T., et al., "Ro 09–1679, A Novel Thrombin Inhibitor", The Journal of Antibiotics, vol. 45, No. 3, Mar. 1992, ppg 424–427.

Krstenansky, J.L., et al., "Development of MDL 28,050, a Small Stable Antithrombin Agent Based on a Functional Domain of the Leech Protein, Hirudin", Thrombosis and Haemostasis, vol. 63, No. 2, 1990, Stuttgart, De.

Kuroda, K., et al., "Fumaric Acid Enhances DNA Synthesis of Rat Hepatocytes by Counter Acting the Toxicities of Mitomycin C and Aflatoxin $B_1$", Jpn. J. Cancer Res. (Gann), Aug. 1986, vol. 77, ppg 750–758.

Kuroda, K., et al., "Inhibitory Effect of *Capsella–bursa–pastoris* extract on Growth of Ehrlich Solid Tumor in Mice", Cancer Research, vol. 36, 1976, Abstract only.

Langlois, M., et al., "Synthesis of symmetrical pseudopeptides as potential inhibitors of the human immunodeficiency virus–1 protease", Eur. J. Med. Chem., vol. 29, 1994, ppg 639–647.

Lehnert, S., et al., "Radiation Response of Drug–Resistant Variants of a Human Breast Cancer Cell Line: The Effect of Glutathione Depletion", Radiation Research, vol. 124, 1990, ppg 208–215.

Miller, A.C., et al., "Posttranscriptional Down–Regulation of ras Oncogene Expression by Inhibitors of Cellular Glutathione", Molecular and Cellular Biology, Jul. 1993, vol. 13, No. 7, ppg 4416–4422.

Mrowietz, U., "Nephrotoxische Wirkung durch Fumarsaure", Hautarzt, 2000–51:615, Springer–Verlag 2000, p. 615. Not translated.

Odom, R. Y., et al., "Cancer Chemoprotective Agents Inhibition of Human HT29 Colon Carcinoma Cell Proliferation is Reversed by N–Acetyl Cysteine", Proceedings of the American Assoc. for Cancer Research Annual, No. 41, Mar. 2000, p. 342, XP008017517.

Ondrus, V., et al., "A Simple Synthesis of Some analogues of Natural Antibiotics", Preliminary Communication, Chem. Papers, 51(3), 1997, ppg 164–166.

Orta, T., et al., "Glutathione manipulation and the radiosensitivity of human tumour and fibroblast cell lines", Int. J. Radiat. Biol., 1995, vol. 68, No. 4, ppg 413–419.

Pearl, J.M., et al., "Fumarate–enriched blood cardioplegia results in complete functional recovery of immature myocardium", Annals of Thoracic Surgery, vol. 57, No. 6, 1994, Abstract only, 1 page.

Peeters, A.J., et al., "Fumaric Acid Therapy for Psoriatic Arthritis. A Randomized, Double–blind, Placebo–controlled Study", British Journal of Rheumatology, vol. XXXI, No. 7, Jul. 1992, ppg 502–504.

Pereira, M.A., et al., "Use of azoxymethane–induced foci of aberrant crypts in rat colon to identify potential cancer chemopreventive agents", Carcinogenesis, vol. 15, No. 5, 1994, ppg 1049–1054.

Portoghese, P.S., et al., "Synthesis and Biological Activity of Analogues of β–Chlornaltrexamine and β–Funaltrexamine at Opioid Receptors", J. of Medicinal Chem., vol. 29, No. 10, 1986, ppg 1861–1864.

Prochaska, H.J., et al., "Elevation of Glutathione Levels by Phase II Enzyme Inducers: Lack of Inhibition of Human Immunodeficiency Virus Type 1 Replication in Chronically Infected Monocytoid Cells", Molecular Pharmacology, vol. 45, No. 5, 1994, ppg 916–921.

Prochaska, H.J., et al., "Oltipraz, an inhibitor of human immunodeficiency virus type 1 replication", Proc. Natl. Acad. Sci., USA, vol. 90, May 1993, ppg 3953–3957.

Rao, C.V., et al., "Chemoprevention of Azoxymethane–Induced Colon Cancer by Ascorbylpalmitate, Carbenoxolone, Dimethylfumarate and p–Methoxyphenol in Male F344 Rats", Anticancer Research, vol. 15, 1995, ppg 1199–1204.

Rao, K.S., et al., "Antihepatotoxic activity of monomethyl fumarate isolated from *Fumaria indica*", Journal of Ethnopharmacology, vol. 60, 1998, ppg 207–213.

Roodnat, J.I., et al., "Akute Niereninsuttizienz bie der Behandlung der Psoriasis mit Fumasaure–Estern", Schweiz. Med., Wschr., vol. 119, nr 2, 1989, ppg 826–830. Not translated.

Rossi, Domenico, et al., "Approach to the Use of Benzylpenicillinacyclase for Configurational Correlations of Amino Compounds. 2. Hydrolysis of N–(p–Aminophenylacetyl) Derivatives of Some Chiral Primary Amines", J. Org. Chem., vol. 44, No. 13, 1979, ppg 2222–2225.

Schirmeister, Tania, "Aziridine–2,3–dicarboxylic Acid Derivatives as Inhibitors of Papain", Arch. Pharm. Pharm. Med. Chem., 329, 1996, ppg 239–244.

Schmidt, K.N, et al., "Anti–psoriatic drug anthralin activates transcription factor NF–kappa–B in murine keratinocytes", Journal of Immunology, vol. 156, 1996, Abstract only.

Spencer, S.R., et al., "Induction of Glutathione Transferases and NAD(P)H:Quinone Reductase by Fumaric Acid Derivatives in Rodent Cells and Tissues", Cancer Research, vol. 50, 1990, ppg 7871–7875.

Steele, V.E., et al., "Preclinical Efficacy Evaluation of Potential Chemopreventive Agents in Animal Carcinogenesis Models: Methods and Results From the NCI Chemoprevention Drug Development Program", J. of Cellular Biochemistry, Supplement 20, 1994, ppg 32–54.

Su, Jean Y.C., et al., "Reduction of $H_2O_2$–evoked, intracellular calcium increases in the rat N18–RE–105 neuronal cell line by pretreatment with an electrophilic antioxidant inducer", Neuroscience Letters, 273, 1999, ppg 109–112.

Subasinghe, Nalin et al., "Synthesis of Acyclic and Dehydroaspartic Acid Analogues of Ac–Asp–Glu–OH and Their Inhibition of Rat Brain N–Acetylated α–linked Acidic Dipeptidase (NAALA Dipeptidase)", Journal of Medicinal Chemistry, vol. 33, No. 10., 1990, ppg 2734–2744.

Vandermeeren, M., et al., "Dimethylfumarate is an Inhibitor of Cytokine–Induced Nuclear Translocation of NF–κB1, But not RelA in Normal Human Dermal Fibroblast Cells", The Journal of Investigative Dermatology, vol. 116, No. 1, Jan. 2001, ppg 124–130.

Vandermeeren, M., et al., "Dimethylfumarate is an Inhibitor of Cytokine–Induced E–Selection, VCAM–1, and ICAM–1 Expression in Human Endothelial Cells", Biochemical and Biophysical Research Communications, vol. 234, 1997, ppg 19–23.

Wang, X., et al., "Enhanced cytoxocity of mitomycin C in human tumour cells with inducers of DT–diaphorase", British Journal of Cancer, vol. 80(8), 1999, ppg 1223–1230.

Weinmann, I., et al., "Influence of Fumaric Acid Derivatives on T Lymphocytes in the Murine Model of HSV–1 Keratitis", IOVS, vol. 41, No. 4, Mar. 15, 2000, XP008017516, ppg S146.

Altmeyer, P. et al., "Systemische Therapie der Psoriasis", T & E Dermatolgie Jg., 1997, vol. 27, ppg. 380–382, 384—not translated.

M. Bacharach–Buhles et al., "Fumaric Acid Esters (FAEs) Suppress CD 15– and ODP 4–positive Cells in Psoriasis", Acta Derm Venerol (Stokh); 1994; Suppl. 186: 79–82.

H. M. Ockenfels et al., "The antipsoricatic agent dimethylfumarate immunomodulates T–cell cytokine secretion and inhibits cytokines of the psoriatic cytokine network", British Journal of Dermatology.

Gasser, et al., "Host Vs Graft and Graft Vs Host Reaction After Allogeneic Heterotopic Small Bowel Transplantation in the Rat", Transplantation Proceedings, vol. 24, No. 3, Jun., 1992, ppg 1128–1129.

Hunziker T., et al.; "Is Psoriasis an Autoimmune Disease", Excerpt from "Therapeutizche Umsehau", Determatological Clinic of the University of Berne; 1993, vol. 50; $2^{nd}$ edition; pp. 110–113.

Nathens, et al., "The Glutathione Depleting Agent Diethylmaleate Prolongs Renal Allograft Survival", Journal of Surgical Research, vol. 77, 1998, ppg 75–79.

Nibbering, P.H. et al., "Intracellular Signalling by Binding Sites for the Antipsoriatic Agent Monomethylfumarate on Human Granulocytes", British J. Dermatol., 1997, vol. 137, ppg. 65–75.

Nibbering, Peter H., "Effects of Monomethylfumarate on Human Granulocytes", Journal of Investigative Dermatology, 1993, vol. 101, ppg. 37–42.

Sebök, Bela et al., "Antiproliferative and Cytotoxic profiles of Antipsoriatic Fumaric Acid Derivatives in Keratinocyte Cultures", European Journal of Pharm., Environ. Toxicol. Pharmacol. Sect., 1994.

Schwinghammer et al., "Pharmacologic prophylaxis of acute graft–versus–host disease after allogeneic marrow transplantation", Therapy Reviews, Clinical Pharmacy, vol. 12, Oct. 1993, ppg 736–761.

Medline Abstract of Bayard et al., "Peroral long–term treatment of psoriasis using fumaric acid derivatives", Hautarzt, May 1987, 38(5), ppg 279–85.

"Merck Manual", 1987, Merck XP–002141006, p. 327, paragraph 2—paragraph 6.

Immunomodulation durch Fumaderm, Das richtungsweisende Konzept, Charité–Berlin, Hautklinik, Symposium, 1.–3. Nov. 1996, 28 pages, 4 page english translation of pp. 23–24.

* cited by examiner

USE OF FUMARIC ACID DERIVATIVES FOR TREATING MITOCHONDRIAL DISEASES

This application is the section 371 national stage of PCT Application PCT/EP00/12504, filed Dec. 11, 2000, the text of which is not in English, which PCT Application claims priority on German Application No. 100 00 577.2, filed Jan. 10, 2000, the text of which is not in English.

TECHNICAL FIELD

The present invention relates to the use of individual fumaric acid derivatives or mixtures thereof for preparing a pharmaceutical composition for treating mitochondrial diseases, especially for treating Parkinson's syndrome, Alzheimer's disease, Chorea Huntington disease, retinopathia pigmentosa and mitochondrial encephalomyopathy.

BACKGROUND

The mitochondria have an independent genetic system of DNA (mtDNA) and RNA and are therefore able to synthesise certain proteins on their own. Both genes of the cell nucleus and the mitochondrial genome code for the components of oxidative phosophorylation and the citrate cycle. A genetic defect of the mtDNA may therefore affect oxidative phosphorylation and the citrate cycle, respectively, and cause malfunctions. Such defects or malfunctions have been associated with the so-called mitochondrial diseases.

Genetic defects of mtDNA may be the result of local mutation by which one base is replaced by another. Such point mutations are associated with neurogenetic myasthenia, ataxia and retinopathia pigmentosa, for example.

Genetic defects of the mtDNA may also be caused by insertion or deletion mutation where one or more nucleotides are inserted into or deleted from the DNA. This mutation mechanism is being discussed in connection with the Kearns Sayre syndrome and the Pearson syndrome.

The mutation of mtDNA also plays a role in neurodegenerative diseases such as Parkinson syndrome, Alzheimer's disease or Chorea Huntington disease (Encyclopedia of Molecular Biology and Molecular Medicine, Vol., 4, Ed. R. A. Meyers). However, it has not been possible to allocate the causative mutations to these diseases without any doubt so far. For example, an accumulation of mutations is also being discussed as a basis of pathogenesis.

The Parkinson syndrome exhibits a number of symptoms which may be divided into three groups. Motoric disorders are expressed by the plus symptoms rigor (increased tonus of the striated musculature) and medium to heavy tremor (twitching in rapid succession) and the minus symptom hypokinesia or akinesia (deterioration of the motor system, loss of postural reflexes). Vegetative symptoms (increased flow of saliva and tears, post-encephalitic seborrhoea) and psychic disorders (increased indecisiveness, depressive moods, etc.) are also being observed.

The disease is based on a destruction of nerve cells in the motoric key areas of the brain stem. In Germany, for example, about 200,000 patients are affected. At molecular level, the Parkinson syndrome is associated, among other things, with mutations of the mitochondrial genome. It has been possible to show mtDNA deletions in Parkinson patients. In addition, a dopamine insufficiency of certain regions of the brain is found in cases of Parkinson syndrome. The symptoms observed are an expression of the impaired balance between the neurohumoral transmitter substances acetyl choline and dopamine.

At present, drug therapies are based on the inhibition of cholinergic neurotransmission with centrally acting anticholinergics, the increase of the dopamine concentration by administration of the dopamine precursor Levodopa and the stimulation of central dopamine receptors with direct dopaminergic agonists.

Specific therapies therefore comprise the administration of anticholinergics or of Levodopa. In order to favourably influence both the plus symptoms and the minus symptom in Parkinson patients, a combination therapy is usually required which is supplemented by non-drug therapeutic measures.

On the other hand, a therapy with anticholinergics is inadvisable for Parkinson patients already suffering from marked psycho-organic disorders or exogenpsychotic symptoms, because a worsening of the symptoms must be expected.

Side effects limiting the therapeutic use of Levodopa are motoric symptoms (hyperkinesia, dyskinesia), vegetative disorders (gastro-intestinal problems, among others) and cardiovascular disorders (such as orthostatic disorders).

Alzheimer's disease is pre-senile or senile dementia which progresses irreversibly and which is characterised by the destruction of areas of the brain. Recent studies show that, in addition to mitochondrial genetic defects, the increased presence of the apolipoprotein $E_4$ (apo $E_4$) is related to the occurrence of Alzheimer's disease. In the hereditary form of this disease, the corresponding gene for the apo $E_4$ is often defective. As opposed to the Parkinson syndrome, no therapy other than treatment with indomethacin is available for Alzheimer's disease. However, indomethacin also has considerable side effects.

Retinopathia pigmentosa is a degenerative process which is more often hereditary than acquired. It is associated with a narrowing of the retinal vessels, opticus atrophy, the destruction of neural elements of the retina and a deposition of pigments. Symptoms are nyctalopia, a severe narrowing of the field of vision and loss of sight.

Mitochondrial encephalomyopathy is a disease characterised by disorders of the mitochondrial respiratory chain. Typical symptoms are myopathy (so-called ragged red fibres myopathy), stunted growth, dementia, epileptic episodes, ataxia, focal neurological disorders and MELAS (mitochondrial encephalomyopathy, lactate acidosis and strokes).

Chorea Huntington is a hereditary dominant autosomal disease with a defect on the short arm of the $4^{th}$ chromosome which usually becomes manifest between the ages of 30 and 50 and is associated with progressive dementia. A defect or atrophy of the *nucleus candatus* and possibly the *nucleus lentiformis* may be named as possible causes. A defect of the neurotransmitter metabolism and the influence of mtDNA defects are under discussion.

BRIEF SUMMARY OF THE INVENTION

Therefore, it is an object of the invention to provide a pharmaceutical composition for the treatment of mitochondrial diseases, especially those described above, and to permit partial treatment of these diseases with drugs, which has not been possible so far. It is another object of the invention to provide a pharmaceutical preparation for the treatment of the above diseases which reduces the side effects of existing drug therapies and does not require a combination therapy.

The object of the present invention is achieved by the use of individual or a mixture of fumaric acid derivative(s) for preparing a pharmaceutical composition for treating mitochondrial diseases, especially for treating Alzheimer's disease, Parkinson's syndrome, Chorea Huntington disease, retinopathia pigmentosa and mitochondrial encephalomyopathy. The subject matters of the invention are characterised in detail in the claims.

FURTHER DETAILED DESCRIPTION OF THE INVENTION

It is known that pharmaceutical preparations which, upon biological degradation after administration, enter into the citric acid cycle or are part thereof gain increasing therapeutic significance—especially when given in high dosages—since they can alleviate or heal diseases caused cryptogenetically.

For example, fumaric acid inhibits the growth of the Ehrlich ascites tumour in mice, reduces the toxic effects of mitomycin C and aflatoxin and displays anti-psoriatic and anti-microbial activity. In general, the treatment of psoriasis with different fumaric acid derivatives has already been described in a number of patents, e.g. EP 0 188 749, DE 25 30 372, DE 26 21 214 or EP 0 312 697.

Another use of certain fumaric acid derivatives, namely of the alkyl hydrogen fumarates, is disclosed in DE 197 21 099.6 and DE 198 53 487.6 according to which these specific fumaric acid derivatives are described for treating auto-immune diseases such as polyarthritis, multiple sclerosis and graft-versus-host reactions. In addition, DE 198 53 487.6 and DE 198 39 566.3 teach the use of alkyl hydrogen fumarates and dialkyl fumarates in transplantation medicine.

Surprisingly, it has now been found that individual fumaric acid derivatives or mixtures thereof may advantageously be used for preparing a pharmaceutical preparation for treating mitochondrial diseases, especially for treating the Parkinson syndrome, Alzheimer's disease, Chorea-Huntington disease, retinopathia pigmentosa or mitochondrial encephalomyopathy.

In the invention, one or more fumaric acid dialkyl esters and/or fumaric acid monoalkyl esters in the form of the free acid or in the salt form are preferably used for preparing the pharmaceutical composition.

The fumaric acid dialkyl esters preferably correspond to the formula:

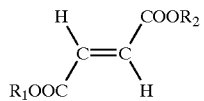

wherein $R_1$ and $R_2$ which may be the same or different independently represent a linear, branched, saturated or unsaturated $C_{1-24}$ alkyl radical or a $C_{5-50}$ aryl radical and wherein these radicals are optionally substituted with halogen (F, Cl, Br, I), hydroxy, $C_{1-4}$ alkoxy, nitro or cyano.

The radicals $R_1$ and $R_2$ preferably are methyl, ethyl, n-propyl, isopropyl, n-butyl, sec-butyl, t-butyl, pentyl, cyclopentyl, 2-ethylhexyl, hexyl, cyclohexyl, heptyl, cycloheptyl, octyl, vinyl, allyl, 2-hydroxyethyl, 2- and/or 3-hydroxypropyl, 2-methoxyethyl, methoxymethyl or 2- or 3-methoxypropyl.

The fumaric acid monoalkyl esters preferably correspond to the formula:

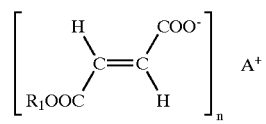

wherein $R_1$ is a radical as defined above; A is hydrogen or an alkaline or alkaline earth metal cation or a physiologically acceptable transition metal cation, preferably selected from $Li^+$, $Na^+$, $K^+$, $Mg^{2+}$, $Ca^{2+}$, $Zn^{2+}$, $Fe^{2+}$, $Mn^{2+}$ and n is 1 or 2 and corresponds to the valence of A.

Preferably the fumaric acid derivatives of the invention are used in such an amount that one dosage unit of the pharmaceutical composition contains an amount of one or more fumaric acid derivative(s) which corresponds or is equivalent to 1 to 500 mg, preferably 10 to 300 mg and most preferably 10 to 200 mg of fumaric acid.

Applications are preferred where the pharmaceutical composition is administered orally, parenterally, rectally, transdermal or ophthally (in the form of eye drops), oral administration being preferred. The preparation is present in the form suitable for the pertinent form of administration.

In case of oral administration the pharmaceutical composition of the invention is present in the form of unit dosage tablets, micro-tablets or micro-tablets (micro-pellets) or granulate which may optionally be encapsulated or filled into sachets, capsules or solutions for drinking.

In a preferred embodiment, solid dosage forms or forms of administration, respectively, are provided with an enteric coating. Such a coating may also be applied to the encapsulated or filled dosage forms.

According to the invention, one or more fumaric acid derivative(s) is/are preferably used which are selected from the group comprising fumaric acid dimethyl ester, fumaric acid diethyl ester, fumaric acid methyl ethyl ester, methyl hydrogen fumarate, ethyl hydrogen fumarate, magnesium methyl fumarate, magnesium ethyl fumarate, zinc methyl fumarate, zinc ethyl fumarate, iron methyl fumarate, iron ethyl fumarate, calcium methyl fumarate and/or calcium ethyl fumarate.

The pharmaceutical composition of the invention may preferably contain 10 to 500 mg of dialkyl fumarate, especially dimethyl fumarate and/or diethyl fumarate; 10 to 500 mg of calcium alkyl fumarate, especially calcium methyl fumarate and/or calcium ethyl fumarate, 0 to 250 mg of zinc alkyl fumarate, especially zinc methyl fumarate and/or zinc ethyl fumarate, 0 to 250 mg of alkyl hydrogen fumarate, especially methyl hydrogen fumarate and/or ethyl hydrogen fumarate and 0 to 250 mg of magnesium alkyl fumarate, especially magnesium methyl fumarate and/or magnesium ethyl fumarate; the total of the amounts specified corresponding to an equivalent of 500 mg, preferably 300 mg and most preferably 200 mg of fumaric acid.

Preferred compositions according to the invention contain only methyl hydrogen fumarate or dimethyl fumarate in an amount of 10 to 300 mg.

For example, the fumaric acid derivatives are prepared according to the method described in EP 0 312 679.

In order to illustrate the use according to the invention, various examples for preparing preferred drugs are given below.

EXAMPLE 1

Preparation of Film Tablets with an Enteric Coating Containing 100.0 mg of Monomethyl Fumarate-Ca Salt, which Corresponds to 78 mg of Fumaric Acid Taking the necessary precautions (breathing mask, gloves, protective clothing, etc.), 10.000 kg of monomethyl fumarate-Ca salt are crushed, mixed intensely and homogenised by means of a sieve 800. Then an excipient mixture of the following composition is prepared: 21.000 kg of starch derivative (STA-RX 1500®), 2.000 kg of micro-crystalline cellulose (Avicel PH 101®), 0.600 kg of polyvinyl pyrrolidone (PVP, Kollidon® 25), 4.000 kg of Primogel®, 0.300 kg of colloidal silicic acid (Aerosil®).

The active ingredient is added to the entire powder mixture, mixed, homogenised by means of a sieve 200 and processed with a 2% aqueous solution of polyvinyl pyrrolidone (PVP, Kollidon® 25) in the usual manner into binder granules, and then mixed with the outer phase in a dry state. The latter consists of 2.000 kg of a so-called FST complex containing 80% of talcum, 10% of silicic acid and 10% of magnesium stearate.

Thereafter the mixture is pressed into convex tablets with a weight of 400 mg and a diameter of 10.0 mm by the usual method. Instead of these classic compaction methods, other methods such as direct compaction or solid dispersions according to the melting and spray drying method may also be used for preparing tablets.

Enteric Coating:

A solution of 2.250 kg of hydroxy propyl methyl cellulose phthalate (HPMCP, Pharmacoat HP® 50) is dissolved in a solvent mixture consisting of 2.50 liters of demineralised water, 13.00 liters of acetone Ph. Helv. VII and 13.00 liters of ethanol (94% by weight) and then 0.240 kg of castor oil (Ph. Eur. II) is added to the solution. The solution is poured or sprayed in portions onto the tablet cores in a coating pan in a conventional manner or applied by means of a fluidised-bed apparatus of the appropriate structure.

After drying, the film coating is applied. Said coating consists of a solution of Eudragit E 12.5%® 4.800 kg, talcum Ph. Eur. II 0.340 kg, titanium(VI) oxide Cronus RN 56® 0.520 kg, coloured lacquer ZLT-2 blue (Siegle) 0.210 kg, and polyethylene glycol 6000 Ph. Helv. VII 0.12 kg in a solvent mixture of 8.200 kg of 2-propanol Ph. Helv. VII, 0.06 kg of glycerine triacetate (Triacetin®) and 0.200 kg of demineralised water. After homogenous distribution in the coating pan or the fluidised bed, the mixture is dried and polished in the usual manner.

EXAMPLE 2

Preparation of Enteric Coated Capsules Containing 86.5 mg of Monoethyl Fumarate-Ca Salt and 110.0 mg of Dimethyl Fumarate, which Corresponds to a Total of 150 mg of Fumaric Acid Taking the necessary precautions (breathing mask, gloves, protective clothing, etc.), 8.650 kg of monoethyl fumarate-Ca salt and 11.000 kg of dimethyl fumarate are intensely mixed with a mixture consisting of 15.000 kg of starch, 6 kg of lactose Ph. Helv. VII, 2 kg of micro-crystalline cellulose (Avicel®), 1 kg of polyvinyl pyrrolidone (Kollidon® 25) and 4 kg of Primogel® and homogenised by means of a sieve 800.

Together with a 2% aqueous solution of polyvinyl pyrrolidone (Kollidon® 25) the entire powder mixture is processed in the usual manner into a binder granulate and mixed with the outer phase in the dried state. Said outer phase consists of 0.350 kg of colloidal silicic acid (Aerosil®), 0.500 kg of Mg stearate and 1.500 kg of talcum Ph. Helv. VII. The homogeneous mixture is then filled in portions of 500.0 mg into appropriate capsules which are then provided with an enteric (gastric-acid resistant) coating consisting of hydroxy propyl ethyl cellulose stearate and castor oil as softening agent by a known method. Instead of hard gelatine capsules, the mixture may also be filled into appropriate gastric acid-resistant capsules, which consist of a mixture of cellulose acetate phthalate (CAP) and hydroxy propyl ethyl cellulose phthalate (HPMCP).

EXAMPLE 3

Preparation of Enteric-coated Micro-tablets in Capsules Containing 87.0 mg of Monoethyl Fumarate-Ca Salt, 120 mg of Dimethyl Fumarate, 5.0 mg of Monoethyl Fumarate-Mg Salt and 3.0 mg of Monoethyl Fumarate-Zn Salt, which Corresponds to a Total of 164 mg of Fumaric Acid ("forte" Tablets)

Taking the necessary precautions (breathing mask, gloves, protective clothing, etc.), 8.700 kg of monoethyl fumarate-Ca salt, 12.000 kg of dimethyl fumarate, 0.500 kg of monoethyl fumarate-Mg salt and 0.300 kg of monoethyl fumarate-Zn salt are crushed, intensely mixed and homogenised by means of an sieve 800. Then an excipient mixture of the following composition is prepared: 18.00 kg of starch derivative (STA-RX 1500), 0.30 kg of micro-crystalline cellulose (Avicel PH 101), 0.75 kg of PVP (Kollidon 120), 4.00 kg of Primogel, 0.25 kg of colloidal silicic acid (Aerosil). The entire powder mixture is added to the active ingredient mixture, homogenised by means of a 200 sieve, processed in the usual manner with a 2% aqueous solution of polyvinyl pyrrolidone (Kollidon K25) to obtain a binder granulate and mixed in a dry state with the outer phase consisting of 0.50 kg of magnesium stearate and 1.50 kg of talcum. Then the powder mixture is pressed by the conventional method into convex micro-tablets with a gross mass of 10.0 mg and a diameter of 2.0 mm. Instead of this classic tabletting method other methods for making tablets such as direct tabletting or solid dispersions by the melt method and the spray drying method may also be used.

The gastric acid-resistant coating may be poured or sprayed on in a classic coating pan or applied in a fluidised-bed apparatus. In order to achieve resistance to gastric acid, portions of a solution of 2.250 kg of hydroxy propyl methyl cellulose phthalate (HPMCP, Pharmacoat HP 50) are dissolved in a mixture of the following solvents: acetone 13.00 l, ethanol 94% by weight denatured with 2% ketone 13.50 l and demineralised water 2.50 l. 0.240 kg of castor oil are added as softening agent to the finished solution and applied in portions to the tablet cores in the usual manner.

Film-coat: After drying is completed, a suspension of the following composition is applied as a film-coat in the same apparatus: talcum 0.340 kg, titanium(VI) oxide Cronus RN 56 0.4 kg, coloured lacquer L red lacquer 86837 0.324 kg, Eudragit E 12.5% 4.800 kg and polyethylene glycol 6000 pH 11 XI 0.12 kg in a solvent mixture of the following composition: 2-propanol 8.170 kg, aqua demineralisata 0.20 kg and glycerine triacetate (Triacetin) 0.600 kg.

The gastric acid-resistant micro-tablets are then filled into hard gelatine capsules at a net weight of 500.0 mg and sealed.

EXAMPLE 4

Example 4 shows the stimulating influence of fumaric acid derivatives on the enzyme activity of succinate dehydrogenase.

Succinate dehydrogenase is part of the mitochondrial membrane and catalyses the dehydration of succinic acid to fumaric acid within the citrate cycle. Hydrogen is passed to the respiratory chain via the electron transfer flavoprotein. Thus, the activity of succinate dehydrogenase may influence the electron flow of the electron transport chain. The latter, in turn, is linked to the process of oxidative phosphorylation, the malfunction of which is considered a cause for mitochondrial diseases. Consequently, the activity of succinate dehydrogenase may also have an effect on oxidative phosphorylation.

The following table 1 shows an evaluation of the stimulating influence of fumaric acid derivatives on the enzyme activity of the succinate dehydrogenase.

| Fumarates | Fibroblasts [0.75 m Val/I] |
|---|---|
| Dimethyl fumarate | strong (838%) |
| Calcium monoethyl fumarate | medium |
| Magnesium monoethyl fumarate | weak |
| Zinc monoethyl fumarate | strong (107%) |
| Monoethyl fumarate | weak |

What is claimed is:

1. A method of treating a patient suffering from a mitochondrial disease, said method comprising administering to said patient a pharmaceutical composition comprising (i) an individual fumaric acid derivative or (ii) a mixture of fumaric acid derivatives, wherein said (i) or (ii) is selected from the group consisting of
   (a) fumaric acid diesters of the formula:

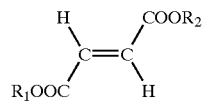

wherein $R_1$ and $R_2$ which may be the same or different independently represent a linear, branched, cyclic, saturated or unsaturated $C_{1-24}$ alkyl radical or a $C_{5-20}$ aryl radical and wherein these radicals are optionally substituted with halogen (F, Cl, Br, I), hydroxy, $C_{1-4}$ alkoxy, nitro or cyano; and
   (b) fumaric acid monoesters of the formula:

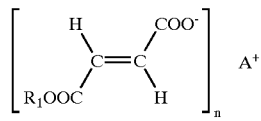

wherein
   $R_1$ is as defined hereinabove,
   A is hydrogen or an alkali or alkaline earth metal cation or a physiologically-acceptable transition metal cation, and
   n is 1 or 2 and corresponds to the valence of A;
   wherein the mitochondrial disease is selected from the group consisting of Parkinson's syndrome, Alzheimer's disease, Chorea Huntington disease, retinopathia pigmentosa, and mitochondrial encephalomyopathy, and wherein one dosage unit of the pharmaceutical composition contains an amount of said fumaric acid derivative(s) which corresponds to 1 to 500 mg of fumaric acid.

2. The method according to claim 1 wherein the fumaric acid derivative(s) in the pharmaceutical composition correspond(s) to the formula of (a).

3. The method according to claim 2 wherein the radicals $R_1$ and $R_2$ are methyl, ethyl, n-propyl, isopropyl, n-butyl, sec-butyl, t-butyl, pentyl, cyclopentyl, 2-ethylhexyl, hexyl, cyclohexyl, heptyl, cycloheptyl, octyl, vinyl, allyl, 2-hydroxyethyl, 2-hydroxypropyl, 3-hydroxypropyl, 2,3-dihydroxypropyl, 2-methoxyethyl, methoxymethyl, 2-methoxypropyl, or 3-methoxypropyl.

4. The method according to claim 1 wherein the fumaric acid derivative(s) in the pharmaceutical composition correspond(s) to the formula of (b).

5. The method according to claim 4 wherein A is one of $Li^\oplus$, $Na^\oplus$, $K^\oplus$, $Mg^{2\oplus}$, $Ca^{2\oplus}$, $Zn^{2\oplus}$, $Mn^{2\oplus}$.

6. The method according to any of claims 1–4 wherein said dosage unit of the pharmaceutical composition contains an amount of fumaric acid derivative(s) which corresponds to 10 to 300 mg of fumaric acid.

7. The method according to any of claims 1–4 wherein said pharmaceutical composition is adapted for and is administered by oral, parenteral, rectal, transdermal or ophthal administration.

8. The method according to any of claims 1–4 wherein said pharmaceutical composition is adapted for and is administered by oral administration.

9. The method according to any of claims 1–4 wherein said pharmaceutical composition is adapted for and is administered by oral administration, and wherein the dosage unit of the pharmaceutical composition administered contains an amount of fumaric acid derivative(s) which corresponds to 10 to 300 mg of fumaric acid.

10. The method according to claim 7 where the pharmaceutical composition for oral administration is present in the form of unit dosage tablets, micro-tablets or micro-pellets optionally encapsulated or filled into sachets, capsules or solutions for drinking.

11. The method according to claim 10 wherein the dosage unit of the pharmaceutical composition administered contains an amount of fumaric acid derivative(s) which corresponds to 10 to 300 mg of fumaric acid.

12. The method according to claim 10 wherein the dosage forms thereof that are solids are provided with an enteric coating.

13. The method according to claim 12 wherein the dosage unit of the pharmaceutical composition administered contains an amount of fumaric acid derivative(s) which corresponds to 10 to 300 mg of fumaric acid.

14. The method according to claim 1 wherein the fumaric acid derivative selected for administration comprises one or more of the following: fumaric acid dimethyl ester, fumaric acid diethyl ester, fumaric acid methyl ethyl ester, methyl hydrogen fumarate, ethyl hydrogen fumarate, calcium methyl fumarate, calcium ethyl fumarate, magnesium methyl fumarate, magnesium ethyl fumarate, zinc methyl fumarate, zinc ethyl fumarate, iron methyl fumarate, iron ethyl fumarate.

15. The method according to claim 1 wherein the dosage units of the pharmaceutical composition contain either individually or in a mixture of any two or more of the following active ingredient(s):

10 to 500 mg of dialkyl fumarate;
10 to 500 mg of calcium alkyl fumarate;
0 to 250 mg of zinc alkyl fumarate;
0 to 250 mg of alkyl hydrogen fumarate;
0 to 250 mg of magnesium alkyl fumarate;

the total amount of the active ingredient(s) administered corresponding to an equivalent of not more than 500 mg of fumaric acid.

16. The method according to claim 15 wherein said total amount of the active ingredient(s) administered corresponds to an equivalent of not more than 300 mg of fumaric acid.

17. The method according to claim 15 wherein said total amount of the active ingredient(s) administered corresponds to an equivalent of not more than 200 mg of fumaric acid.

18. The method according to claim 1 wherein the dosage units of the pharmaceutical composition contain either individually or in a mixture of any two or more of the following active ingredient(s):

10 to 500 mg of dimethyl fumarate and/or diethyl fumarate;

10 to 500 mg of calcium methyl fumarate and/or calcium ethyl fumarate;

0 to 250 mg of zinc methyl fumarate and/or zinc ethyl fumarate;

0 to 250 mg of methyl hydrogen fumarate and/or ethyl hydrogen fumarate;

0 to 250 mg of magnesium methyl fumarate and/or magnesium ethyl fumarate;

the total amount of the active ingredient(s) administered corresponding to an equivalent of not more than 500 mg of fumaric acid.

19. The method according to claim 18 wherein said total amount of the active ingredient(s) administered corresponds to an equivalent of not more than 300 mg of fumaric acid.

20. The method according to claim 18 wherein said total amount of the active ingredient(s) administered corresponds to an equivalent of not more than 200 mg of fumaric acid.

21. The method according to claim 18 wherein said active ingredient is dimethyl fumarate, or diethyl fumarate, or both, and wherein said active ingredient is in the form of unit dosage tablets, micro-tablets or micro-pellets.

22. The method according to claim 21 wherein said active ingredient(s) is dimethyl fumarate.

* * * * *

UNITED STATES PATENT AND TRADEMARK OFFICE
CERTIFICATE OF CORRECTION

PATENT NO. : 6,858,750 B2
DATED : February 22, 2005
INVENTOR(S) : Rajendra K. Joshi and Hans-Peter Strebel It is certified that error appears in the above-identified patent and that said Letters Patent is hereby corrected as shown below:

<u>Title page,</u>
Item [56], References Cited, FOREIGN PATENT DOCUMENTS, reads "RU 5189813 9/2000" and should read -- RU 2189813 9/2000 --.

Signed and Sealed this

Twenty-eighth Day of March, 2006

JON W. DUDAS
*Director of the United States Patent and Trademark Office*